US011102588B2

(12) United States Patent
Schumaier

(10) Patent No.: US 11,102,588 B2
(45) Date of Patent: Aug. 24, 2021

(54) HEARING AID DRYER AND DISINFECTION KIT

(71) Applicant: Daniel R. Schumaier, Elizabethton, TN (US)

(72) Inventor: Daniel R. Schumaier, Elizabethton, TN (US)

( * ) Notice: Subject to any disclaimer, the term of this patent is extended or adjusted under 35 U.S.C. 154(b) by 0 days.

(21) Appl. No.: 16/671,480

(22) Filed: Nov. 1, 2019

(65) Prior Publication Data

US 2021/0044907 A1 Feb. 11, 2021

Related U.S. Application Data

(63) Continuation-in-part of application No. 16/532,868, filed on Aug. 6, 2019.

(51) Int. Cl.
*H04R 25/00* (2006.01)
*A61L 2/10* (2006.01)

(52) U.S. Cl.
CPC ............... *H04R 25/00* (2013.01); *A61L 2/10* (2013.01); *H04R 2460/17* (2013.01)

(58) Field of Classification Search
CPC combination set(s) only.
See application file for complete search history.

(56) References Cited

U.S. PATENT DOCUMENTS

| 5,404,105 | A | 4/1995 | Chari |
| 5,640,783 | A | 6/1997 | Schumaier |
| 5,852,879 | A * | 12/1998 | Schumaier ............... A61L 2/07 34/80 |
| D414,304 | S | 9/1999 | Schumaier |
| D467,394 | S | 12/2002 | Schumaier |
| 7,062,057 | B2 | 6/2006 | Wu |
| D536,491 | S | 2/2007 | Schumaier |
| 7,182,820 | B2 | 2/2007 | Campbell et al. |
| 7,195,177 | B2 * | 3/2007 | Haws ..................... G05D 22/02 236/44 A |
| 8,112,900 | B2 | 2/2012 | Romanek |
| 9,709,327 | B2 | 7/2017 | Marchiori |
| 9,839,707 | B2 * | 12/2017 | Won .......................... A61L 2/10 |
| 9,843,870 | B2 | 12/2017 | Naumann |

(Continued)

FOREIGN PATENT DOCUMENTS

| CN | 201018665 | 2/2008 |
| CN | 103747388 A | 4/2014 |

(Continued)

OTHER PUBLICATIONS

Ear Technology Corporation, Dry & Store Global Operation, Oct. 2005, pp. 1-7. (Year: 2005).*

*Primary Examiner* — Fan S Tsang
*Assistant Examiner* — Angelica M McKinney
(74) *Attorney, Agent, or Firm* — Luedeka Neely Group, P.C.

(57) ABSTRACT

A portable airtight electronic component dryer device includes a container having an interior portion for receiving one or more electronic components for drying and a removable lid for the container. A desiccant is disposed in the interior portion of the container. The removable lid contains a disinfecting light source and a power source for providing power to the disinfecting light source. Light generated by the disinfecting light source is directed into the interior portion of the container.

29 Claims, 4 Drawing Sheets

(56) References Cited

U.S. PATENT DOCUMENTS

| | | | |
|---|---|---|---|
| 2003/0196687 A1* | 10/2003 | Campbell | F26B 9/003 |
| | | | 134/35 |
| 2004/0073275 A1 | 4/2004 | Maltan et al. | |
| 2004/0118427 A1* | 6/2004 | Palfy | A61C 17/036 |
| | | | 134/1 |
| 2004/0258559 A1 | 12/2004 | Paskal et al. | |
| 2005/0189354 A1* | 9/2005 | Heather | B65D 51/145 |
| | | | 220/288 |
| 2006/0220620 A1 | 10/2006 | Aradachi et al. | |
| 2009/0080679 A1* | 3/2009 | Rass | H04R 1/12 |
| | | | 381/322 |
| 2009/0296968 A1* | 12/2009 | Wu | H04R 25/00 |
| | | | 381/323 |
| 2010/0088916 A1 | 4/2010 | Romanek | |
| 2012/0006995 A1* | 1/2012 | Greuel | C02F 1/325 |
| | | | 250/373 |
| 2012/0216418 A1 | 8/2012 | Serman et al. | |
| 2013/0004367 A1 | 1/2013 | Roberts | |
| 2014/0175280 A1* | 6/2014 | Tantillo | A61L 2/10 |
| | | | 250/338.1 |
| 2015/0162770 A1 | 6/2015 | Choi et al. | |
| 2015/0174426 A1 | 6/2015 | Germain et al. | |
| 2015/0250646 A1* | 9/2015 | Lipford | A61K 45/06 |
| | | | 424/613 |
| 2016/0074545 A1 | 3/2016 | Kim | |
| 2016/0165367 A1 | 6/2016 | Ochsenbein | |
| 2016/0277848 A1 | 9/2016 | Naumann | |
| 2016/0301287 A1 | 10/2016 | Nagata et al. | |
| 2017/0023299 A1 | 1/2017 | Leung et al. | |
| 2017/0347473 A1* | 11/2017 | Freer | B01D 53/0454 |
| 2018/0123355 A1 | 5/2018 | Olson et al. | |
| 2018/0123367 A1 | 5/2018 | Higgins et al. | |
| 2019/0167827 A1* | 6/2019 | Gaska | A61L 2/24 |
| 2019/0208342 A1 | 7/2019 | Higgins et al. | |
| 2019/0297437 A1* | 9/2019 | Gil | F26B 9/003 |

FOREIGN PATENT DOCUMENTS

| | | | | |
|---|---|---|---|---|
| CN | 203589776 U | | 5/2014 | |
| CN | 104534822 A | | 4/2015 | |
| CN | 205457846 | * | 8/2016 | A47G 21/00 |
| CN | 205901402 U | | 1/2017 | |
| CN | 208770000 | * | 4/2019 | A61B 50/31 |
| DE | 202017107151 U1 | | 1/2018 | |
| KR | 20060012144 A | | 2/2006 | |
| KR | 20120085980 A | | 8/2012 | |
| KR | 101466886 B1 | | 12/2014 | |
| WO | 2007066908 A1 | | 6/2007 | |

\* cited by examiner

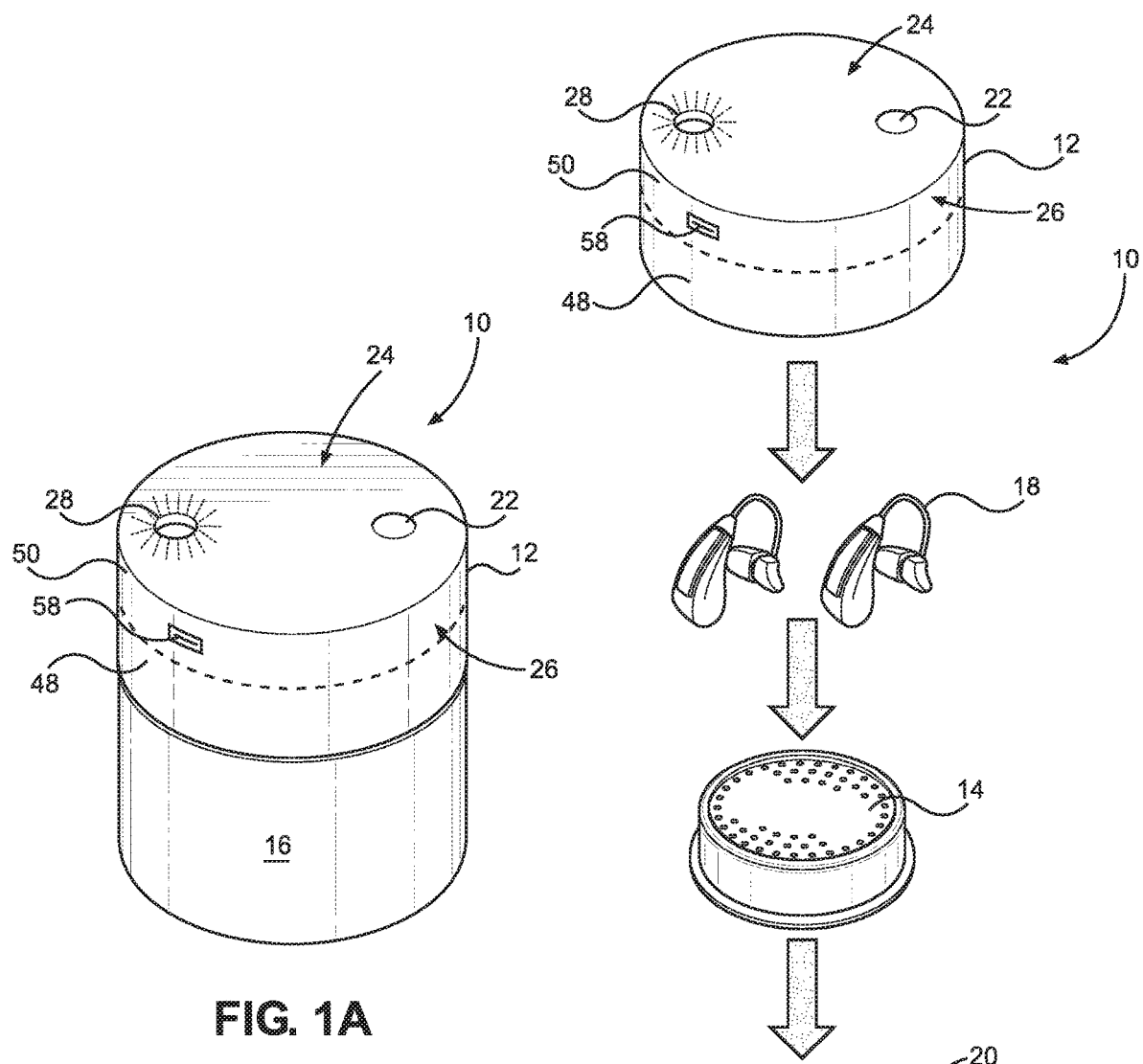
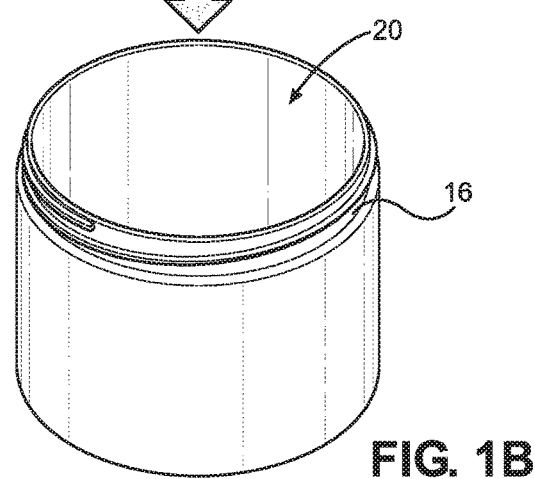
FIG. 1A
FIG. 1B

HEARING AID DRYER AND DISINFECTION KIT

RELATED APPLICATIONS

This application claims priority as a continuation-in-part of U.S. patent application Ser. No. 16/532,868 titled HEARING AID DRYER AND DISINFECTION KIT, filed Aug. 6, 2019, the entire contents of which are incorporated herein by reference.

TECHNICAL FIELD

The disclosure relates to a portable drying device for drying electronic and nonelectronic components, and in particular to a hearing aid drying and disinfection kit.

BACKGROUND AND SUMMARY

A hearing aid patient relies on a hearing aid device, and thus its components, to reliably function. Hearing aid devices comprise numerous sensitive electronic components that require periodic maintenance. These components may include a receiver, microphone, volume control, potentiometers, contacts, rechargeable batteries, and circuitry.

Hearing aid devices are subject to a moist environment when worn by a user. Moisture alone may negatively impact device performance and longevity particularly with regard to the electronic components. Moisture also aggravates the buildup of ear wax, dirt, and grime, which may also deteriorate performance and longevity.

Untreated moisture may, for example, cause corrosion on contacts, potentiometers, circuitry, batteries, and wires, condensation on screens or diaphragms in the microphone/receiver, and/or loss of sensitivity of or change in the frequency response of the microphone/receiver. Further, untreated moisture and buildup may lead to ear infections.

Reducing moisture content and/or facilitating the removal of buildup and bacteria, assists in the reliable functionality, maintainability, cleanliness, and longevity of hearing aid devices and prevents unwanted ear infections. Many hearing aid maintenance systems are rather large and expensive and may not be conveniently carried in a purse, suitcase, or brief-case. Accordingly, there is a need for a simple, relatively small, portable, battery-powered, and inexpensive hearing aid maintenance kit that reduces moisture and disinfects the hearing aids.

In view of the foregoing, an embodiment of the disclosure provides an electronic component dryer device including a container having an interior portion for receiving one or more electronic components for drying, a desiccant disposed in the interior portion of the container, and a removable lid for the container. The removable lid contains a disinfecting light source, and a power source for providing power to the disinfecting light source. Light generated by the disinfecting light source is directed into the interior portion of the container.

In another embodiment there is provided an improved electronic component dryer kit that includes an air-tight container and a removable desiccant. The improvement includes a removable lid for the container, wherein the removable lid contains a disinfecting light source, and a power source for providing power to the disinfecting light source. The light generated by the disinfecting light source is directed into the interior portion of the container.

In some embodiments, the removable lid includes a controller circuit that is isolated from the interior portion of the container, wherein the controller circuit controls the disinfecting light source to operate for a predetermined period of time. In other embodiments, the predetermined period of time can be controlled by firmware in the processor to range from minutes to hours.

In some embodiments, wherein the removable lid also includes a switch that is isolated from the interior portion of the container for activating the disinfecting light source. In other embodiments, the switch comprises a capacitive switch. In still other embodiments, the capacitive switch is on a top portion of the removable lid.

In some embodiments, the disinfecting light source comprises an ultraviolet light source. In other embodiments, the ultraviolet light source includes one more ultraviolet light emitting diodes or one or more ultraviolet lamps.

In some embodiments, the removable lid also includes a power on/off indicator.

In some embodiments, the removable lid is an air-tight removable lid.

In some embodiments, the desiccant is a replaceable desiccant holder containing desiccant and having vent holes therein.

In some embodiments, the dryer device includes lid removal detection circuitry comprising a magnetic switch or metal contacts on the container and the lid that closes a circuit to provide power to the disinfecting light source when lid is secured to the container.

In some embodiments, the controller circuit generates an indication that the desiccant is due for replacement.

In some embodiments, the dryer device includes an indicator lamp disposed on the removable lid, and the indication that the desiccant is due for replacement comprises changing a property of light generated by the indicator lamp.

BRIEF DESCRIPTION OF THE DRAWINGS

The invention will be further understood from the drawings herein of certain preferred embodiments, wherein the structures are not drawn to scale, and the following description thereof, wherein:

FIG. 1A is a perspective view, not to scale, of a hearing aid dryer and disinfection kit according to the disclosure.

FIG. 1B is an exploded, perspective view, not to scale, of the hearing aid dryer and disinfection kit of FIG. 1A.

DESCRIPTION OF THE PREFERRED EMBODIMENTS

Figure 2A:
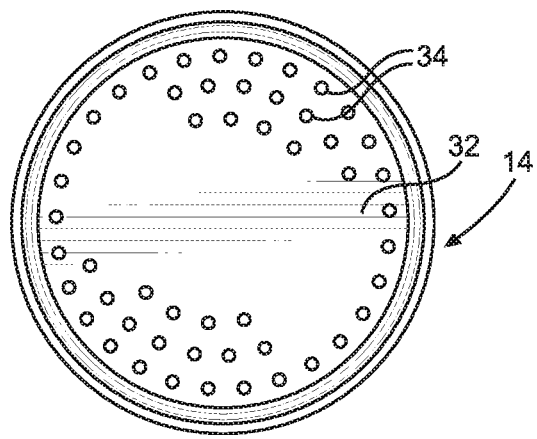
FIG. 2A is a plan, top view of a removable desiccant for the hearing aid dryer and disinfection kit according to FIG. 1A.

With reference to FIGS. 1A and 1B there are illustrated a perspective view and an exploded view, not to scale, of an electronic component dryer and disinfection device 10 showing the primary components thereof. In various embodiments, the device 10 may be used to dry and disinfect various types of electronic components, including but not limited to hearing aids, personal sound amplifiers, ear buds, and in-ear monitors. The device 10 includes a removable lid 12, a removable desiccant holder 14 containing desiccant, and a container 16 for holding hearing aids 18 to be dried and disinfected. An interior 20 of the container 16 is sized to contain the desiccant holder 14 and the hearing aids 18 during a drying and disinfection procedure. The disinfection procedure is initiated by a cycle start switch 22 on a top portion 24 or side portion 26 of the lid 12. During the disinfection procedure, an indicator lamp 28 attached to the lid 12, such as an LED lamp, may be illuminated to warn a user not to remove the lid 12 of the device 10 until the disinfection step is completed.

The lid 12, desiccant holder 14 and container 16 may have a cylindrical shape to facilitate a screw-on or snap-on lid 12. However, any other shaped container, lid and desiccant holder may be used including square or rectangular shaped lids, desiccant holders and containers. The lid 12 may also provide an air-tight seal when attached to the container 16 so that ambient moisture external to the device 10 is avoided. An O-ring type gasket may be included for the purpose of providing the air-tight seal.

Figure 2B:
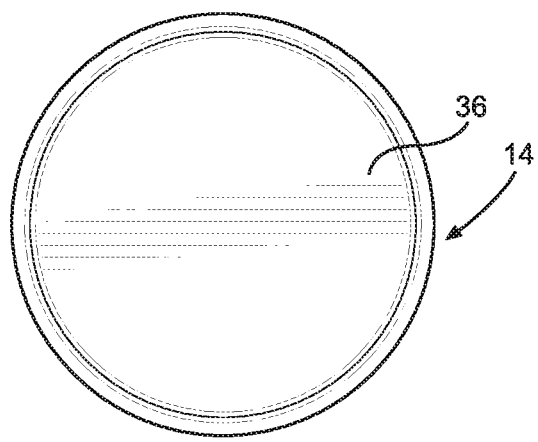
FIG. 2B is a plan, bottom view of a removable desiccant for the hearing aid dryer and disinfection kit according to FIG. 1A.

FIG. 2A is a top, plan view, of the desiccant holder 14 containing desiccant. The desiccant may include any moisture absorbing material such as supported granular CaO, CaCl2, ZnCl2, CUSO4, silica gel or the like. The amount of desiccant in the desiccant holder 14 may be sufficient to dry hearing aids for a month or more. A top side 32 of the desiccant holder 14 has a plurality of vent holes 34 therein for transferring moisture from the hearing aids 18 to desiccant in the desiccant holder 14. A bottom side 36 of the desiccant holder 14, as shown in FIG. 2B is devoid of vent holes.

Figure 3:
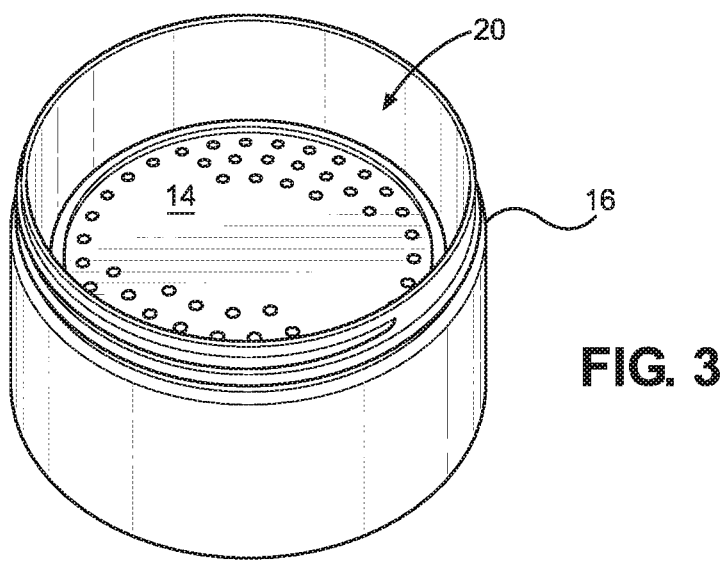
FIG. 3 is a perspective view of a container for the hearing aid dryer and disinfection kit of FIG. 1A with a removable desiccant disposed in the container.
Figure 4:
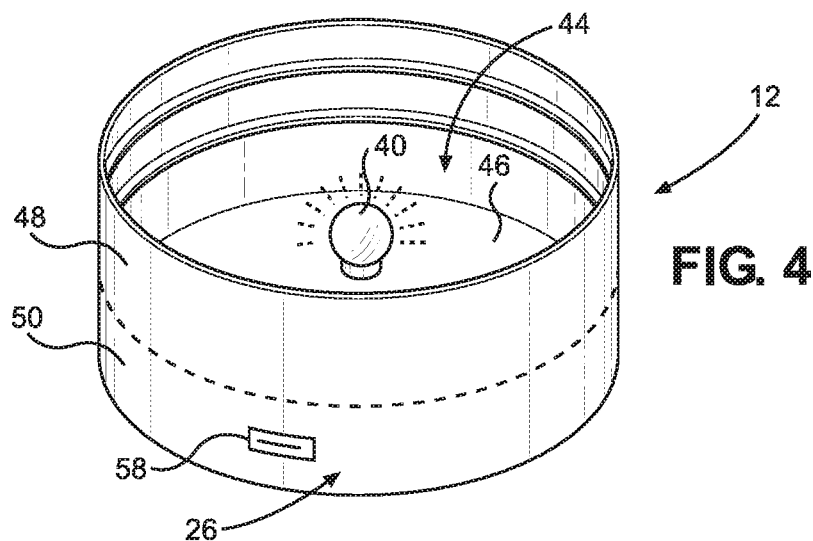
FIG. 4 is a perspective view of an inside portion of the lid for the container of FIG. 3.
Figure 5:
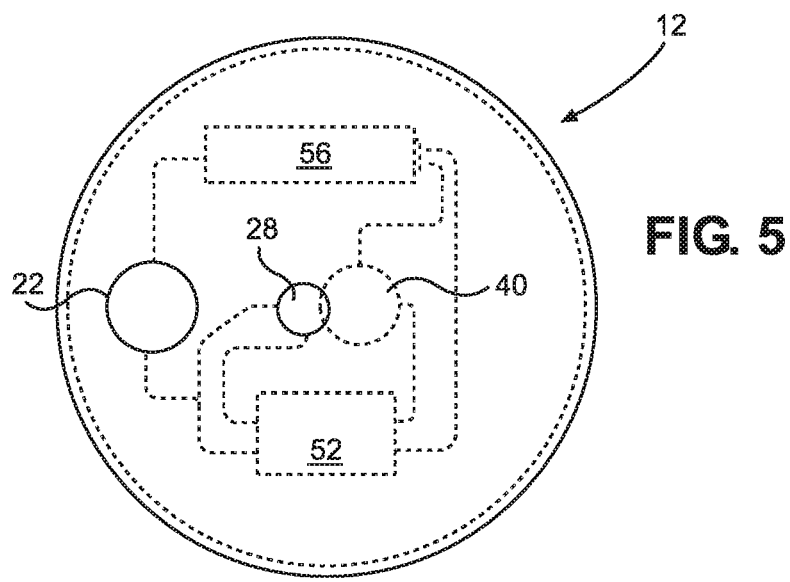
FIG. 5 is a plan view, not to scale, of electrical components within the lid of FIG. 4.
Figure 6:
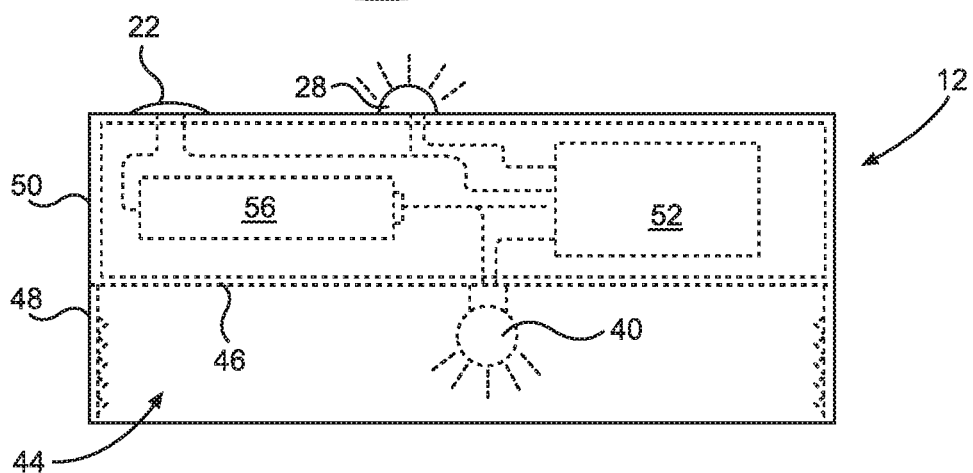
FIG. 6 is an elevational, cross-sectional view of the lid of FIGS. 4 and 5.

FIG. 3 illustrates the desiccant holder 14 disposed in the interior 20 of the container 16. The container 16 has an overall interior size that is suitable for accommodating the desiccant holder 14 and one or more hearing aids 18 therein to be dried and disinfected. In some embodiments, the desiccant may be spherical in shape and disposed in a bottom portion of the container 16 with or without a separate desiccant holder 14. In some embodiments, the container 16 may be a two part container having desiccant disposed in bottom portion of the container and the hearing aids 18 disposed in a top portion of the container wherein the hearing aids 18 are separated from the desiccant by a foraminous separator. In other embodiments, the hearing aids 18 may be disposed in direct contact with the desiccant in the absence of a desiccant holder.

Figure 7:
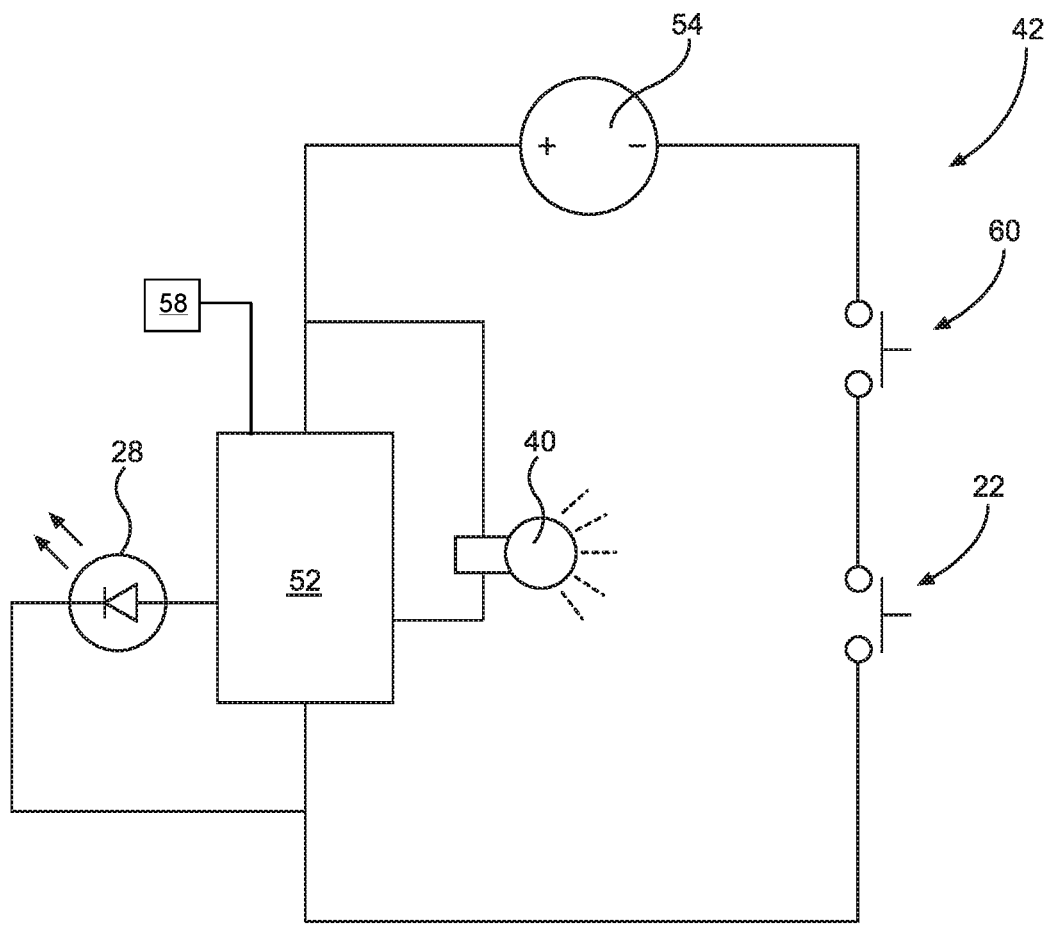
FIG. 7 is a schematic drawing of a control system for the hearing aid dryer and disinfection kit according to FIG. 1A.

An important feature of the hearing aid dryer and disinfection device 10 is the lid 12. Non-limiting aspects of the lid 12 are illustrated in FIGS. 4-7 and include a disinfecting light source, such as an ultraviolet (UV) light source 40, and controller circuitry 52 therefor (FIG. 7). The UV light source 40 is disposed in an interior 44 of the lid 12 on a partition 46 that separates an interior portion 48 of the lid 12 from an electronic housing portion 50 of the lid 12. The UV light source 40 may provide direct irradiation of the hearing aids 18 to kill bacteria or the like on surfaces of the hearing aids 18. Also, ozone may be produced by the UV light source 40 to act as a deodorizer.

A suitable UV light source 40 is a UV-C lamp that is a high intensity 50 mm linear (253.7 nm) germicidal lamp rated at 70 uW/cm$^2$. The wavelength of 253.7 nanometers of the UV-C lamp is proven to inhibit colony formation in microorganisms which may significantly reduce itching and infection of the ear canal. In some embodiments, the disinfecting light source produces violet light in the 400-450 nm range to generate Reactive Oxygen Species (ROS) for killing bacteria.

In some embodiments, the UV light source 40 comprises one or more UV light emitting diodes (LEDs). In a preferred embodiment, multiple UV LEDs are distributed across the bottom surface of the lid 12 to evenly illuminate the interior 20 of the container 16.

The interior portion 48 of the lid 12 and the interior 20 of the container 16 may include a UV reflective coating or may be formed from a UV reflective material, such as e-PTFE (expanded polytetrafluoroethylene).

As set forth above, the indicator lamp 28 on the lid 12 is visible to the user and when illuminated indicates that the UV light source 40 is activated to warn the user not to open the lid 12 of the device 10 while the UV light source 40 is on. In a preferred embodiment, the indicator lamp 28 is a light-emitting diode (LED). The controller circuitry 52 may be activated by pressing the switch 22 which may be a capacitive switch or a micro-contact switch. If a capacitive switch is used, the lid 12 is devoid of any moving parts.

The controller circuitry 52 also includes a digital timer for controlling the illumination of the UV lamp 40 for a predetermined amount of time. The predetermined amount of time may range from a few minutes to several hours or longer.

A power source 54 (FIG. 7) such as a rechargeable or standard battery 56 may be included in the electronic housing portion 50 of the lid 12 to power the controller circuit 52, UV light source 40, and LED lamp 28. In some embodiments, a rechargeable battery is used as the power source 54 which may be charged by removing the battery 56 from the lid 12 or by means of a USB connection 58 disposed on the side portion 26 of the lid 12. In some embodiments, the power source 54 is provided through the USB connection 58 in the absence of an internal battery 56.

Many of the structural components of the device 10, including the lid 12, desiccant holder 14 and the container 16 may be made of a durable plastic material. In some embodiments, the container 16 may be made of glass or ceramic.

As shown in FIG. 7, some embodiments of the device 10 include lid removal detection circuitry 60 to detect that the lid 12 has been removed from the container, in which case the UV light source 40 is deactivated. The detection circuitry 60 may comprise a magnetic switch or metal contacts on the threads of the lid 12 and the container 16 that close the circuit powering the UV light source 40 when lid 12 is screwed down tightly.

It will be appreciated that the desiccant in the desiccant holder 14 loses its effectiveness after some number of drying cycles. In a preferred embodiment, the device 10 provides a reminder to the user when it is time to replace the desiccant holder 14 with a fresh one. To implement the reminder, the controller 52 counts the number of drying/disinfection cycles that have occurred since the most recent replacement of the desiccant holder 14. For example, if it is assumed that the device 10 will be used once a day for drying and disinfection, and if it is assumed that the desiccant holder 14 should be replaced at least every thirty days, then the device 10 should provide a change-out reminder after a particular desiccant holder 14 has been used in thirty drying/disinfection cycles.

In a preferred embodiment, the controller 52 increments a counter each time the cycle start switch 22 is pressed while the lid 12 is closed. When the counter reaches the change-out threshold count, such as thirty, the controller 52 generates an indication to the user that it is time to change out the desiccant holder 14. In one embodiment, the change-out indication comprises the indicator lamp 28 changing colors, such as from green to red. In an alternative embodiment, the change-out indication comprises a beeping tone or other audible indicator.

In some embodiments, the change-out reminder is provided in two stages. For example, the controller 52 may generate an initial change-out indication at 21 days into the drying/disinfection cycle, such as by changing the indicator lamp 28 from green to yellow, and then generate a final change-out indication at 30 days into the drying/disinfection cycle, such as by changing the indicator lamp 28 from yellow to red.

After the desiccant holder 14 has been replaced, and while the lid 12 is still open, the user may press and hold the cycle start switch 22, such as for five seconds, to cause the controller 52 to reset the cycle count to zero and change the indicator lamp 28 back to green.

In a preferred embodiment, the change-out threshold count is a programmable value that may be changed as needed depending on the characteristics of desiccant holder 14 in use. For example, if the manufacturer of the desiccant holder 14 increases the useful lifetime of the desiccant in the holder 14, the change-out threshold count may be reprogrammed to accommodate a greater number of cycles before the change-out reminder is generated. In some embodiments, the change-out threshold count may be reprogrammed in memory of the controller 52 via the USB connection 58, such as by using a software application running on a mobile computing device, such as a smart phone.

The invention has been described in detail with particular reference to preferred embodiments thereof, but it will be understood that variations and modifications will be affected with the spirit and scope of the invention.

What is claimed is:

1. A portable electronic component dryer device comprising:
    a container having an interior portion for receiving one or more electronic components for drying;
    a desiccant disposed in the interior portion of the container; and
    a removable lid for the container, the removable lid comprising:
        an ultraviolet disinfecting light source,
        a controller circuit that is isolated from the interior portion of the container, wherein the controller circuit generates an indication that the desiccant is due for replacement based on a programmable change-out threshold count, and
        a battery for providing power to the ultraviolet disinfecting light source and the controller circuit,
        wherein light generated by the ultraviolet disinfecting light source is directed into the interior portion of the container.

2. The electronic component dryer device of claim 1, wherein the controller circuit controls the ultraviolet disinfecting light source to operate during a predetermined period of time.

3. The electronic component dryer device of claim 2, wherein the controller circuit activates the ultraviolet disinfecting light source for the predetermined period of time ranging from minutes to hours.

4. The electronic component dryer device of claim 1, wherein the removable lid further comprises a switch that is isolated from the interior portion of the container, the switch for activating the ultraviolet disinfecting light source.

5. The electronic component dryer device of claim 4, wherein the switch comprises a capacitive switch.

6. The electronic component dryer device of claim 5, wherein the capacitive switch is on a top portion of the removable lid.

7. The electronic component dryer device of claim 1, wherein the ultraviolet disinfecting light source comprises one or more ultraviolet light emitting diodes or one or more ultraviolet lamps.

8. The electronic component dryer device of claim 1, wherein the container comprises a cylindrical container.

9. The electronic component dryer device of claim 1, wherein the removable lid is an air-tight removable lid.

10. The electronic component dryer device of claim 1, wherein the desiccant comprises a replaceable desiccant holder containing desiccant and having vent holes therein.

11. The electronic component dryer device of claim 1, wherein the change-out threshold count is reprogrammed by a software application running on a mobile computing device.

12. The electronic component dryer device of claim 1 further comprising an indicator lamp disposed on the removable lid, wherein the indication comprises changing a property of light generated by the indicator lamp.

13. An improved electronic component dryer kit comprising an air-tight container having an interior portion and a removable desiccant disposed within the interior portion, the improvement comprising:
    a removable lid for the container, the removable lid comprising:
        a disinfecting light source,
        a controller circuit that is isolated from the interior portion of the container, wherein the controller circuit generates an indication that the desiccant is due for replacement based on a programmable change-out threshold count, and
        a battery for providing power to the disinfecting light source and the controller circuit,
    wherein light generated by the disinfecting light source is directed into the interior portion of the container.

14. The improved electronic component dryer kit of claim 13, wherein the controller circuit controls the disinfecting light source to operate during a predetermined period of time.

15. The improved electronic component dryer kit of claim 14, wherein the controller circuit activates the disinfecting light source for the predetermined period of time ranging from minutes to hours.

16. The improved electronic component dryer kit of claim 13, wherein the removable lid further comprises a switch that is isolated from the interior portion of the container, the switch for activating the disinfecting light source.

17. The improved electronic component dryer kit of claim 16, wherein the switch comprises a capacitive switch on a top portion of the removable lid.

18. The improved electronic component dryer kit of claim 13, wherein the disinfecting light source comprises an ultraviolet light source.

19. The improved electronic component dryer kit of claim 18, wherein the ultraviolet light source comprises one or more ultraviolet light emitting diodes or one or more ultraviolet lamps.

20. The improved electronic component dryer kit of claim 13, wherein the container comprises a cylindrical container.

21. The improved electronic component dryer kit of claim 13, wherein the removable lid is an air-tight removable lid.

22. The improved electronic component dryer kit of claim 13, wherein the desiccant comprises a replaceable desiccant holder containing desiccant and having vent holes therein.

23. The electronic component dryer device of claim 13, wherein the change-out threshold count is reprogrammed by a software application running on a mobile computing device.

24. The electronic component dryer device of claim 13 further comprising an indicator lamp disposed on the removable lid, wherein the indication comprises changing a property of light generated by the indicator lamp.

25. A portable electronic component dryer device comprising:
- a container having an interior portion for receiving one or more electronic components for drying;
- a desiccant disposed in the interior portion of the container;
- an air-tight removable lid for the container, the removable lid comprising:
  - a disinfecting light source,
  - a controller circuit that is isolated from the interior portion of the container, wherein the controller circuit generates an indication that the desiccant is due for replacement based on a programmable change-out threshold count,
  - a battery for providing power to the disinfecting light source and the controller circuit, and
  - lid removal detection circuitry that removes power from the disinfecting light source upon removal of the lid from the container,
- wherein light generated by the disinfecting light source is directed into the interior portion of the container.

26. The portable electronic component dryer device of claim 25 wherein the lid removal detection circuitry comprises a magnetic switch or metal contacts on the container and the lid that closes a circuit between the battery and the disinfecting light source when lid is secured to the container.

27. The portable electronic component dryer device of claim 25 wherein the lid includes threads that engage corresponding threads on the container, and wherein the removal detection circuitry comprises metal contacts on the threads of the container and metal contacts on the threads on the lid that close a circuit between the battery and the disinfecting light source when lid is secured to the container.

28. A portable electronic component dryer device comprising:
- a container having an interior portion for receiving one or more electronic components for drying;
- a desiccant disposed in the interior portion of the container; and
- a removable lid for the container, the removable lid comprising:
  - a disinfecting light source that generates light directed into the interior portion of the container when the removable lid is attached to the container;
  - a battery for providing power to the disinfecting light source; and
  - a controller circuit for controlling the disinfecting light source to operate during a predetermined period of time and for generating an indication that the desiccant is due for replacement based on a programmable change-out threshold count.

29. The electronic component dryer device of claim 28 further comprising an indicator lamp disposed on the removable lid, wherein the indication comprises changing a property of light generated by the indicator lamp.

\* \* \* \* \*